(12) United States Patent
Caracci et al.

(10) Patent No.: US 7,999,944 B2
(45) Date of Patent: Aug. 16, 2011

(54) MULTI-CHANNEL SWEPT WAVELENGTH OPTICAL INTERROGATION SYSTEM AND METHOD FOR USING SAME

(75) Inventors: Stephen J. Caracci, Elmira, NY (US); Michael J. Dailey, Jr., Painted Post, NY (US); William J. Miller, Horseheads, NY (US); Robert A. Modavis, Painted Post, NY (US); Deepti J. Mudaliar, Horseheads, NY (US); David A. Pastel, Horseheads, NY (US); Michael B. Webb, Lindley, NY (US); Qi Wu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 264 days.

(21) Appl. No.: 12/256,852

(22) Filed: Oct. 23, 2008

(65) Prior Publication Data

US 2010/0105148 A1 Apr. 29, 2010

(51) Int. Cl.
*G01N 21/55* (2006.01)
(52) U.S. Cl. ............................. 356/448; 356/445
(58) Field of Classification Search .................. None
See application file for complete search history.

(56) References Cited

U.S. PATENT DOCUMENTS

| | | | | |
|---|---|---|---|---|
| 4,545,250 | A | 10/1985 | Miwa | 73/602 |
| 4,815,843 | A | 3/1989 | Tiefenthaler et al. | 356/128 |
| 4,818,886 | A | 4/1989 | Drucker | 250/566 |
| 6,633,593 | B2 * | 10/2003 | Ksendzov et al. | 372/20 |
| 6,677,873 | B2 | 1/2004 | Berezin | 341/131 |
| 6,785,433 | B2 | 8/2004 | Tiefenthaler | 385/12 |
| 7,170,599 | B2 * | 1/2007 | Cunningham et al. | 356/326 |
| 7,239,395 | B2 | 7/2007 | Gollier | 356/445 |
| 7,346,233 | B2 * | 3/2008 | Gollier et al. | 385/12 |
| 7,790,406 | B2 * | 9/2010 | Cunningham et al. | 435/7.2 |

(Continued)

FOREIGN PATENT DOCUMENTS

EP 1 031 828 9/2000

(Continued)

OTHER PUBLICATIONS

K. Cottier et al., "Label-free highly sensitive detection of (small) molecules by wavelength interrogation of integrated optical chips", Sensors and Actuators B, 2003, vol. 91, pp. 241-251.

(Continued)

*Primary Examiner* — Gregory J Toatley
*Assistant Examiner* — Juan D Valentin
(74) *Attorney, Agent, or Firm* — Gregory B. Butler; Thomas R. Beall

(57) ABSTRACT

A multi-channel swept wavelength optical interrogation system and a method are described herein that enable the interrogation of one or more biosensors which for example could be located within the wells of a microplate. In one embodiment, the optical interrogation system comprises: (a) a tunable laser that emits an optical beam which has a predetermined sequence of distinct wavelengths over a predetermined time period; (b) a distribution unit that splits the optical beam into a plurality of interrogation beams; (c) an array of optical interrogation units that receive and direct the interrogation beams towards an array of biosensors; (d) the array of optical interrogation units receive a plurality of reflected interrogation beams from the array of biosensors; (e) a data processing device that receives and processes information associated with the reflected interrogation beams to determine for example whether or not there was a biochemical interaction on anyone of the biosensors.

21 Claims, 9 Drawing Sheets

U.S. PATENT DOCUMENTS

| | | | |
|---|---|---|---|
| 2003/0059820 A1 | 3/2003 | Vo-Dinh | 435/6 |
| 2003/0059855 A1* | 3/2003 | Cunningham et al. | 356/319 |
| 2003/0138020 A1 | 7/2003 | Chen | 372/75 |
| 2004/0263841 A1 | 12/2004 | Caracci et al. | 356/300 |
| 2005/0044519 A1 | 2/2005 | Sengupta et al. | 716/11 |
| 2005/0227374 A1 | 10/2005 | Cunningham | 436/518 |
| 2005/0264818 A1 | 12/2005 | Gollier | 356/445 |
| 2006/0017923 A1 | 1/2006 | Ruchti et al. | 356/326 |
| 2006/0141527 A1 | 6/2006 | Caracci et al. | 435/7.1 |
| 2006/0141611 A1 | 6/2006 | Frutos et al. | 435/287.2 |
| 2006/0180750 A1 | 8/2006 | Gollier et al. | 250/227.11 |
| 2006/0274314 A1* | 12/2006 | Thomsen et al. | 356/445 |
| 2007/1002068 | 1/2007 | Caracci et al. | 435/7.1 |
| 2007/0031291 A1* | 2/2007 | Piech et al. | 422/82.05 |
| 2007/0154356 A1* | 7/2007 | Modavis | 422/102 |
| 2007/0237685 A1 | 10/2007 | Bergman et al. | 422/102 |
| 2007/0276608 A1 | 11/2007 | Gollier et al. | 702/19 |
| 2008/0204760 A1 | 8/2008 | Gollier et al. | 356/484 |
| 2008/0247907 A1 | 10/2008 | Bergman et al. | 422/68.1 |
| 2009/0046292 A1* | 2/2009 | Mirsky et al. | 356/445 |

FOREIGN PATENT DOCUMENTS

| | | |
|---|---|---|
| EP | 1 236 807 | 9/2002 |
| WO | 2004/083820 | 9/2004 |
| WO | 2004/092730 | 10/2004 |

OTHER PUBLICATIONS

T. Farrell et al., "Tunable laser technology for sensing applications", Physics and Applications of Optoelectronic Devices, Proceedings of SPIE, 2004, vol. 5594, pp. 66-80.

J.P. Golden et al., "A Comparison of Imaging Methods for Use in an Array Biosensor", Biosensors and Bioelectronics, vol. 17, 2002, pp. 719-725.

C.E. Jordan et al., "Surface Plasmon Resonance Imaging Measurements of DNA Hybridization Adsorption and Streptavidin/DNA Multilayer Formation at Chemically Modified Gold Surfaces", Anal. Chem, 1997, vol. 69, pp. 4939-4947.

J.M. Jung et al., "A Fusion Protein Expression Analysis Using Surface Plasmon Resonance Imaging", Analytical Biochemistry, vol. 330, 2004, pp. 251-256.

V. Kanda et al., "Label-Free Reading of Microarray-Based Immunoassays With Surface Plasmon Resonance Imaging", Anal. Chem., 2004, vol, 76, pp. 7257-7262.

J.P. Landry et al., "Label-Free Detection of Microarrays of Biomolecules by Oblique-Incidence Reflectivity Difference Microscopy", Optics Letters, Mar. 15, 2004, vol, 29, No. 6, pp. 581-583.

P.Y. Li et al., "A New Method for Label-Free Imaging of Biomolecular Interactions", Sensors and Actuators B, vol. 99, 2004, pp. 6-13.

C.R. Mace et al., "Theoretical and Experimental Analysis of Arrayed Imaging Reflectometry as a Sensitive Proteomics Technique", Anal. Chem., 2006, vol. 78, pp. 5578-5583.

Ph.M. Nellen et al., "Integrated Optical Input Grating Couplers as Biochemical Sensors", Sensors and Actuators, vol. 15, 1988, pp. 285-295.

M. Piliarik et al., "A New Surface Plasmon Resonance Sensor for High-Throughput Screening Applications", Biosensor and Bioelectronics, vol. 20, 2005, pp. 2104-2110.

K. Tiefenthaler et al., "Integrated Optical Switches and Gas Sensors", Apr. 1984, Optics Letters, vol. 10, No. 4, pp. 137-139.

Z.H. Wang et al., "A Label-Free Multisensing Immunosensor Based on Imaging Ellipsometry", Anal. Chem., 2003, vol. 75, pp. 6119-6123.

G.J. Wegner et al., "Characterization and Optimization of Peptide Arrays for the Study of Epitope—Antibody Interactions Using Surface Plasmon Resonance Imaging", Anal. Chem., 2002, vol, 74, pp. 5161-5168.

G.J. Wegner et al., "Real-Time Surface Plasmon Resonance Imaging Measurements for the Multiplexed Determination of Protein Adsorption/Desorption Kinetics and Surface Enzymatic Reactions on Peptide Microarrays", Anal. Chem., 2004, vol. 76, pp. 5677-5684.

M. Wiki et al., "Novel integrated optical sensor based on a grating coupler triplet", Biosensor & Bioelectronics, vol. 13, 1998, pp. 1181-1185.

H.P. Zappe et al., "Narrow-linewidth vertical-cavity surface-emitting lasers for oxygen detection", Applied Optics, May 20, 2000, vol. 39, No. 15, pp. 2475-2478.

* cited by examiner

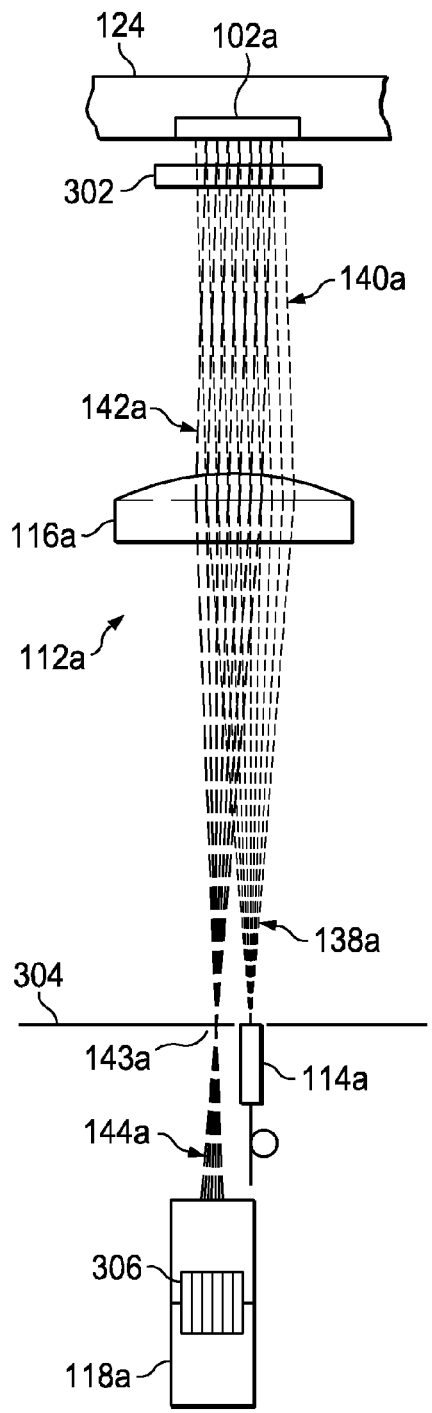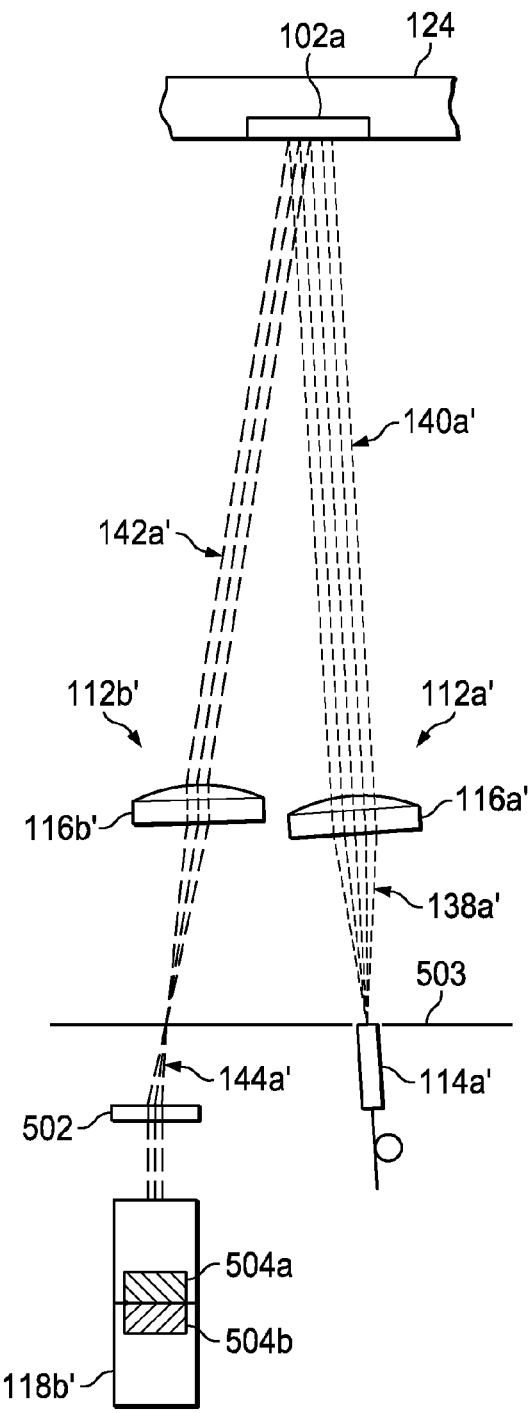
FIG. 3
FIG. 5

US 7,999,944 B2

MULTI-CHANNEL SWEPT WAVELENGTH OPTICAL INTERROGATION SYSTEM AND METHOD FOR USING SAME

TECHNICAL FIELD

The present invention relates to a multi-channel swept wavelength optical interrogation system and a method for using the multi-channel swept wavelength optical interrogation system to interrogate one or more biosensors which for example could be located within the wells of a microplate.

BACKGROUND

Today non-contact optical sensor technology is used in many areas of biological research to help perform increasingly sensitive and time-constrained assays. In one application, an optical interrogation system can be used to monitor changes in the refractive index or variations in the optical response-optical resonance of a biosensor as a biological substance is brought into a sensing region of the biosensor. The presence of the biological substance alters the optical resonance of the biosensor when it causes a bio-chemical interaction like material binding, adsorption etc..... It is this alteration of the optical resonance that enables one to use the biosensor to directly monitor a biological event in label-free assays. Examples of biosensors include surface plasmon resonance (SPR) sensors and waveguide grating coupler (WGC) sensors. A detailed discussion about the structure and function of the WGC sensor is provided in the following documents:

U.S. Pat. No. 4,815,843 entitled "Optical Sensor for Selective Detection of Substances and/or for the Detection of Refractive Index Changes in Gaseous, Liquid, Solid and Porous Samples".
K. Tiefenthaler et al. "Integrated Optical Switches and Gas Sensors" Opt. Lett. 10, No. 4, April 1984, pp. 137-139.
Ph. M. Nellen, K Tiefenthaler, W. Lukosz, "Integrated Optical Input Grating Couplers as Biochemical Sensors" Sensors and Actuators, 15, 273 (1988).
The contents of these documents are incorporated by reference herein.

The optical interrogation system used today to interrogate the biosensor can take many forms, and two of the more general forms are briefly described next. In one case, the optical interrogation system delivers a single-wavelength, high-angular content optical beam to the biosensor, and the output beam received from the biosensor provides some information about the angular response of the biosensor. This type of optical interrogation system is commonly referred to as an angular interrogation system since angular detection is employed to locate a dominant angle in the output beam which is indicative of the particular optical response-optical resonance of the biosensor. In another case, the optical interrogation system delivers a collimated optical beam containing a range of wavelengths to the biosensor, the output beam received from the biosensor provides some information about the wavelength response of the biosensor. This type of optical interrogation system is commonly referred to as a spectral interrogation system since the spectrum of the output beam is analyzed to locate the resonant wavelength which is indicative of the particular optical response-optical resonance of the biosensor.

These types of optical interrogation systems work relatively well but there is still a desire to try and design a new and improved optical interrogation system that can be used to interrogate a biosensor and determine if a biomolecular binding event (e.g., binding of a drug to a protein) or if some other event occurred on a surface or very near the surface of the biosensor. Accordingly, there has been and is a need for a new and improved optical interrogation system that can be used to interrogate a biosensor. This need and other needs have been satisfied by the multi-channel swept wavelength optical interrogation system and interrogation method of the present invention.

SUMMARY

In one aspect, the present invention includes an optical interrogation system that comprises: (a) a tunable laser that emits an optical beam which has a predetermined sequence of distinct wavelengths over a predetermined time period; (b) a distribution unit that splits the optical beam into a plurality of interrogation beams; (c) an array of optical interrogation units that receive and direct the interrogation beams towards an array of biosensors; (d) the array of optical interrogation units receive a plurality of reflected interrogation beams from the array of biosensors; (e) a data processing device that receives and processes information associated with the reflected interrogation beams to determine for example whether or not there was a biochemical interaction on anyone of the biosensors.

In another aspect, the present invention includes a method for interrogating one or more biosensors where the method includes the steps of: (a) emitting an optical beam which has a predetermined sequence of distinct wavelengths over a predetermined time period; (b) splitting the optical beam into one or more interrogation beams; (c) directing the one or more interrogation beams towards one or more biosensors; (d) receiving one or more reflected interrogation beams from the one or more biosensors; and (e) processing information associated with the reflected interrogation beams to determine for example whether or not there was a biochemical interaction on anyone of the biosensors.

Additional aspects of the invention will be set forth, in part, in the detailed description, figures and any claims which follow, and in part will be derived from the detailed description, or can be learned by practice of the invention. It is to be understood that both the foregoing general description and the following detailed description are exemplary and explanatory only and are not restrictive of the invention as disclosed.

BRIEF DESCRIPTION OF THE DRAWINGS

A more complete understanding of the present invention may be had by reference to the following detailed description when taken in conjunction with the accompanying drawings wherein:

FIG. 3 illustrates in greater detail an optical interrogation unit that is incorporated within the optical interrogation system shown in FIG. 1 in accordance with an embodiment of the present invention;

FIG. 5 illustrates in greater detail two optical interrogation units that are incorporated within the optical interrogation system shown in FIG. 4 in accordance with an embodiment of the present invention;

DETAILED DESCRIPTION

Figure 1:
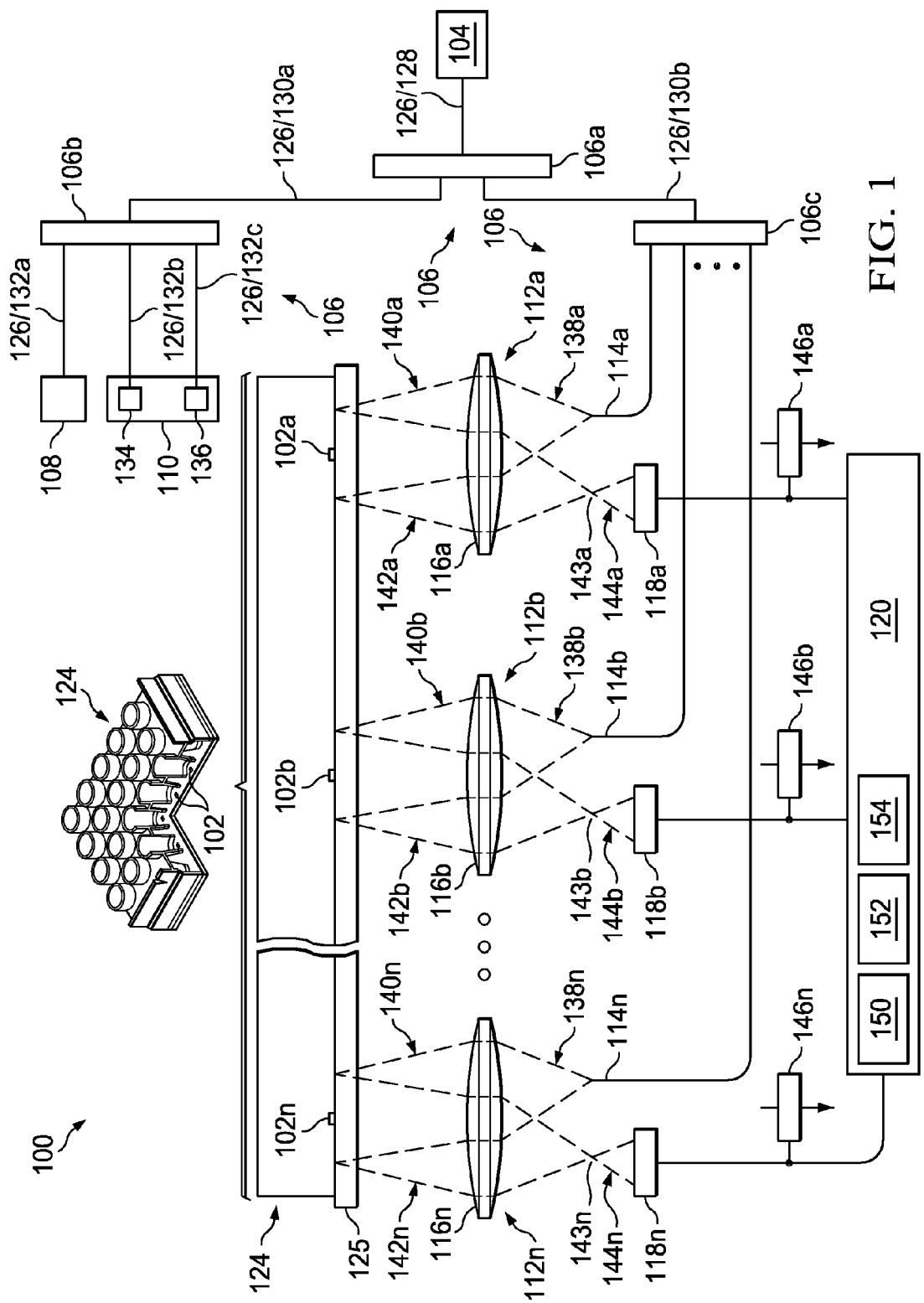
FIG. 1 is a block diagram of an exemplary optical interrogation system which is configured to interrogate one or more biosensors in accordance with an embodiment of the present invention.

Referring to FIG. 1, there is a block diagram illustrating the basic components of an exemplary optical interrogation system 100 which is configured to interrogate one or more biosensors 102a, 102b ... 102n in accordance with an embodiment of the present invention. The exemplary optical interrogation system 100 includes a tunable laser 104, a distribution unit 106 (e.g., 1×2 splitter 106a, a 1×3 splitter 106b and a 1×N splitter 106c), a power tracking device 108, a wavelength tracking device 110, N-optical interrogation units 112a, 112b ... 112n (e.g., N-fiber launches 114a, 114b ... 114n, N-lenses 116a, 116b ... 116n (e.g., N-doublets 116a, 116b ... 116n) and N-photo detectors 118a, 118b ... 118n (or N-multiple element photo detectors 118a, 118b ... 118n)) and a data processing device 120. A discussion about different ways the optical interrogation system 100 can be used to interrogate the biosensors 102a, 102b ... 102n is provided below with respect to methods 1000 and 1200 (see FIGS. 10 and 12).

In FIG. 1, the biosensors 102a, 102b ... 102n are shown located within the wells 122 of a microplate 124 which is typically used to perform static endpoint biochemical assays. For a detailed discussion about an exemplary microplate 124, reference is made to the co-assigned U.S. Patent Application Publication No. 2007-0220689 A1 (the contents of which are incorporated by reference herein). Alternatively, the biosensors 102a, 102b ... 102n can be located within the wells (or flow chambers) of a closed flow-through microplate (not shown) which is typically used to perform kinetic biochemical assays. For a detailed discussion about an exemplary closed flow-through microplate, reference is made to the co-assigned U.S. Pat. No. 7,824,624 and the co-assigned U.S. Patent Application Publication No. 2008-0247907 A1 (the contents of which are incorporated by reference herein). In one embodiment, the microplate 124 (including the closed flow-through microplate) can be placed on a holder 125 which supports the microplate 124 (e.g., see FIG. 7 which illustrates a holder 125 that has masks 702 formed therein).

The tunable laser 104 (e.g., swept wavelength tunable laser 104) emits an optical beam 126 which has a predetermined sequence of distinct wavelengths over a predetermined time period. For instance, the tunable laser 104 can have a tuning range where the emitted optical beam 126 sequences through 838 nm to 853 nm without mode hop at a tuning speed up to 1000 nm/sec. The tunable laser 104 is shown emitting the optical beam 126 into a fiber optic cable 128 which is connected to the 1×2 splitter 106a. In this example, the 1×2 splitter 106a receives the optical beam 126 and splits-forwards the optical beam 126 to the 1×3 splitter 106b and the 1×N splitter 106c respectively on fiber optic cables 130a and 130b. The 1×3 splitter 106b receives the optical beam 126 and splits the optical beam 126 into a fiber optic cable 132a which is connected to the power tracking device 108. Plus, the 1×3 splitter 106b receives the optical beam 126 and splits the optical beam 126 into fiber optic cables 132b and 132c which are connected to the wavelength tracking device 110.

The power tracking device 108 tracks the changing power of the optical beam 126 that is emitted from the tunable laser 104. In one embodiment, the power tracking device 108 has a photodiode which monitors the optical power variation as the tunable laser 104 tunes across the wavelength range during the predetermined time period. The changing power data is used by the data processing device 120 as a power reference to remove the effect of power variations in the output of the spectra from the interrogated biosensor(s) 102a, 102b ... 102n. In particular, the data processing device 120 uses the changing power data to normalize the optical power detected by the photo detectors 118a, 118b ... 118n to obtain the correct grating reflectivity of the biosensors 102a, 102b ... 102n. In addition, the data processing device 120 can use the changing power data to calibrate the spectral dependence of the optical splitters 106a, 106b and 106c (e.g., fused fiber couplers 106a, 106b and 106c).

The wavelength tracking device 110 tracks the changing wavelengths of the optical beam 126 emitted from the tunable laser 104. In particular, the wavelength tracking device 110 measures the wavelength of the tunable laser 104 at each instant when the wavelength is swept over the tuning range. In one embodiment, the wavelength tracking device 110 is based on optical interferometry and includes a fiber Mach-Zehnder interferometer (MZI) 134 and an etalon 136. The fiber MZI 134 is used to decode the instantaneous wavelength of the optical beam 126 to a very high resolution during the operation of the tunable laser 104. The etalon 136 is used to provide an accurate reference of the wavelength of the optical beam 126 during the operation of the tunable laser 104.

Figure 2A:
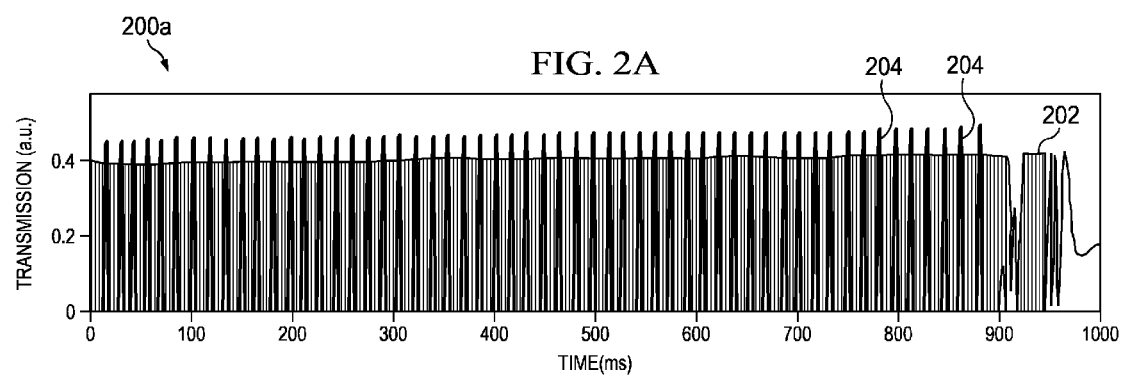
FIGS. 2A and 2B are graphs that illustrate the output from a fiber MZ interferometer and the output from an etalon which are part of a wavelength tracking device that is incorporated within the optical interrogation system shown in FIG. 1 in accordance with an embodiment of the present invention.
Figure 2B:
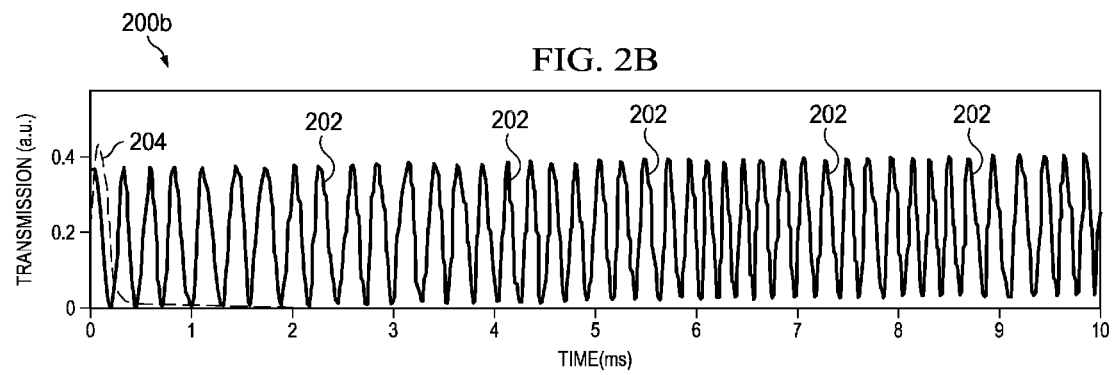

Referring to FIGS. 2A and 2B, there are two graphs 200a and 200b illustrating the output 202 from the photodiode of the fiber MZI 134 and the output 204 from the etalon 136 where the graph 200a has a 1 second time scale and the graph 200b has a 10 ms time scale. The periodicity or "free spectral range" (FSR) of the fiber MZI 134 is determined by:

$$FSR = \frac{c}{n_g \Delta L} \quad (1)$$

where ΔL is the path length difference between interfering beams and $n_g$ is the optical group index in the optical path. By properly designing the path length difference of the fiber MZI 134, the FSR can be designed to be smaller than 1 pm. In practice, a fiber MZI 134 with a path length difference of 30 mm would have a FSR of 16 pm which would provide sufficient precision for wavelength measurement. Alternatively, the wavelength tracking device 110 instead of using the fiber MZI 134 could incorporate other types of optical interferometers like, for example, a free space Michaelson interferometer, a free space Mach-Zhender interferometer or a free space Fabry-Perot interferometer.

The etalon 136 can be an air or a vacuum spaced etalon 136 which uses a low Coefficient Thermal Expansion (CTE) spacer material that exhibits a very high thermal stability. In one embodiment, this spacer material can be a titania silicate glass such as the type sold under the brand name of Corning ULE® (Corning Code 7972 Ultra Low Expansion Glass). The shift of the etalon 136 transmission peaks 204 due to the thermal expansion of the spacer material can be represented as follows:

$$\frac{d\upsilon}{dT} = \frac{\upsilon}{FSR} \frac{d(FSR)}{dT} = \upsilon \cdot CTE \quad (2)$$

where CTE=10 ppb/K for Corning ULE® substrate. This translates to a shift of less than 10 fm/K in the features of the etalon 136. In practice, the thermal performance of this type of assembled etalon 136 is not going to be limited by the CTE of the spacer material when the vendor specified stability is 30 MHz/K or 71 fm/K. Thus, the etalon 136 when used in a laboratory environment does not require temperature control to meet the current requirements associated with tracking the wavelength of the emitted optical beam 126. If the etalon 136 is located in a temperature controlled chamber, then a conventional solid etalon 136 could be used. Alternatively, a gas or atomic absorption cell with calibrated absorption lines can be employed to reference the wavelength of the emitted optical beam 126.

The etalon 136 has an output 204 that is used as the trigger signal to start the acquisition of the data during the interrogation process of the biosensors 102a, 102b . . . 102n. In this way, the beginning wavelength of the emitted optical beam 126 is precisely defined and the changing wavelength of the emitted optical beam 126 can at any moment of the sweep be calculated by measuring the number of oscillations in the output 202 from the MZI 134 relative to the output 204 of the etalon 136. Thus, the wavelength tracking device 110 effectively combines the MZI 134 and a stable wavelength reference like the etalon 136 to provide both measurement accuracy and precision when tracking the wavelength of the optical beam 126 emitted from the tunable laser 104. An alternative way for tracking the changing wavelengths of the optical beam 126 that could also be used herein was discussed in a co-assigned U.S. Pat. No. 7,599,055 (the contents of which are hereby incorporated by reference herein).

Referring back to FIG. 1, the 1×2 splitter 106a forwards the optical beam 126 on fiber optic cable 130b to the 1×N splitter 106c. The 1×N splitter 106c interfaces with the N-fiber launches 114a, 114b . . . 114n (e.g., N single-mode fibers 114a, 114b . . . 114n) where each fiber launch 114a, 114b . . . 114n outputs an optical beam 138a, 138b . . . 138n towards a corresponding lens 116a, 116bc . . . 116n (e.g., collimating/imaging doublet 116a, 116b . . . 116n). The lenses 116a, 116b . . . 116n respectively collimate the optical beams 138a, 138b . . . 138n and direct the collimated optical beams 140a, 140b . . . 140n to illuminate and preferably overfill the corresponding biosensors 102a, 102b . . . 102n. In addition, the lenses 116a, 116b, 116c . . . 116n respectively receive the optical beams 142a, 142b, 142c . . . 142n that are reflected from the corresponding biosensors 102a, 102b . . . 102n. The lenses 116a, 116b, 116c . . . 116n respectively focus the reflected optical beams 142a, 142b . . . 142n which are then allowed to diverge beyond the focal points 143a, 143b . . . 143c of the lenses 116a, 116b . . . 116n before the defocused optical beams 144a, 144b . . . 144n are incident upon the corresponding detectors 118a, 118b . . . 118n. Alternatively, the detectors 118a, 118b . . . 118n could be placed ahead of the focal points 143a, 143b . . . 143n so they can receive the defocused optical beams 144a, 144b . . . 144n.

The detectors 118a, 118b . . . 118n generate a sequence of intensity spot patterns 146a, 146b . . . 146n from the respective biosensors 102a, 102b . . . 102n where each of the intensity spot patterns 146a, 146b . . . 146n corresponds with one of the distinct wavelengths of the optical beam 126 that was emitted from the tunable laser 104. For instance, detector 118a generates a sequence of intensity spot patterns 146a of the illuminated biosensor 102a where each intensity spot pattern 146a corresponds with one of the distinct wavelengths of the optical beam 126 (and optical beam 138a) that was emitted from the tunable laser 104 (and the fiber launch 114a). The data processing device 120 receives and processes the collected intensity spot patterns 146a, 146b . . . 146n to determine for example whether or not there was a biochemical interaction or some other event that occurred on one or more of the biosensors 102a, 102b . . . 102n or to calibrate a uniformity of surface chemistry and target molecule immobilizations on the one or more biosensors 102a, 102b . . . 102n.

Alternatively, the tunable laser 104 could emit an optical beam 126 that is distributed to the optical interrogation units 112a, 112b . . . 112n using free space splitters or diffractive optics instead of the aforementioned fiber optic splitter 106c. If the fiber optic splitter 106c is used then the optical beam 126 could be passed through a polarization scrambler (not shown in FIG. 1) to eliminate the polarization effects of the single mode fibers 114a, 114b . . . 114n. FIG. 3 illustrates in greater detail one optical interrogation unit 112a which includes the single mode fiber launch 114a that emits optical beam 138a at lens 116a (collimating optic 116a) which emits a collimated optical beam 140a that passes through a polarizer 302 (optional) and illuminates a transverse magnetic (TM) mode in the biosensor 102a. The biosensor 102a reflects a collimated optical beam 142a which passes back through the polarizer 302 and the lens 116a (collection optic 116a) where a defocused optical beam 144a is incident upon a photo detector 118a. The polarizer 302 if used would typically be placed at least 10 mm away from the fiber launch 114a, so that the optical beam 138a, 140a, 142a or 144a is sufficiently diverged when impinging upon the polarizer 302. In this way, defects on the polarizer 302, if any, have little effect on the optical beams 138a, 140a, 142a and 144a.

In this exemplary optical interrogation unit 112a, the fiber launch 114a is located on the launch plane 304 and the photo detector 118a is located near an image plane which is located below the focal point 143a while the lens 116a is located about 20 mm from the fiber launch 114a and the biosensor 102a is located about 12 mm from the lens 116a. The focal length of the collimating lens 116a determines the size of the interrogation beam 140*a* that is incident upon the grating of the biosensor 102*a*. Thus, with a focal length of 20 mm, for example, the spot size of the interrogation optical beam 140*a* on the biosensor 102*a* is 4 mm, which would overfill the grating on the biosensor 102*a* and make the interrogation less sensitive to the positional variation of the microplate 124. Plus, the photo detector 118*a* in this example is a single element photo detector 118*a* but it could be a multiple element photo detector 118*a* if the biosensor 102*a* had both a sample region and a reference region (see FIG. 5). The single element photo detector 118*a* is typically used within a non-reference interrogation optics design in which the biosensor 102*a* has just a sample region and not a reference region. In this case, the reflected defocused interrogation optical beam 144*a* would be incident on a single photodiode 306 which for instance has a size of at least 1×1 mm$^2$ within the photo detector 118*a*. Also, in this case, a plate holder 125 that does not have masks could be used to support the microplate 124.

Figure 4:
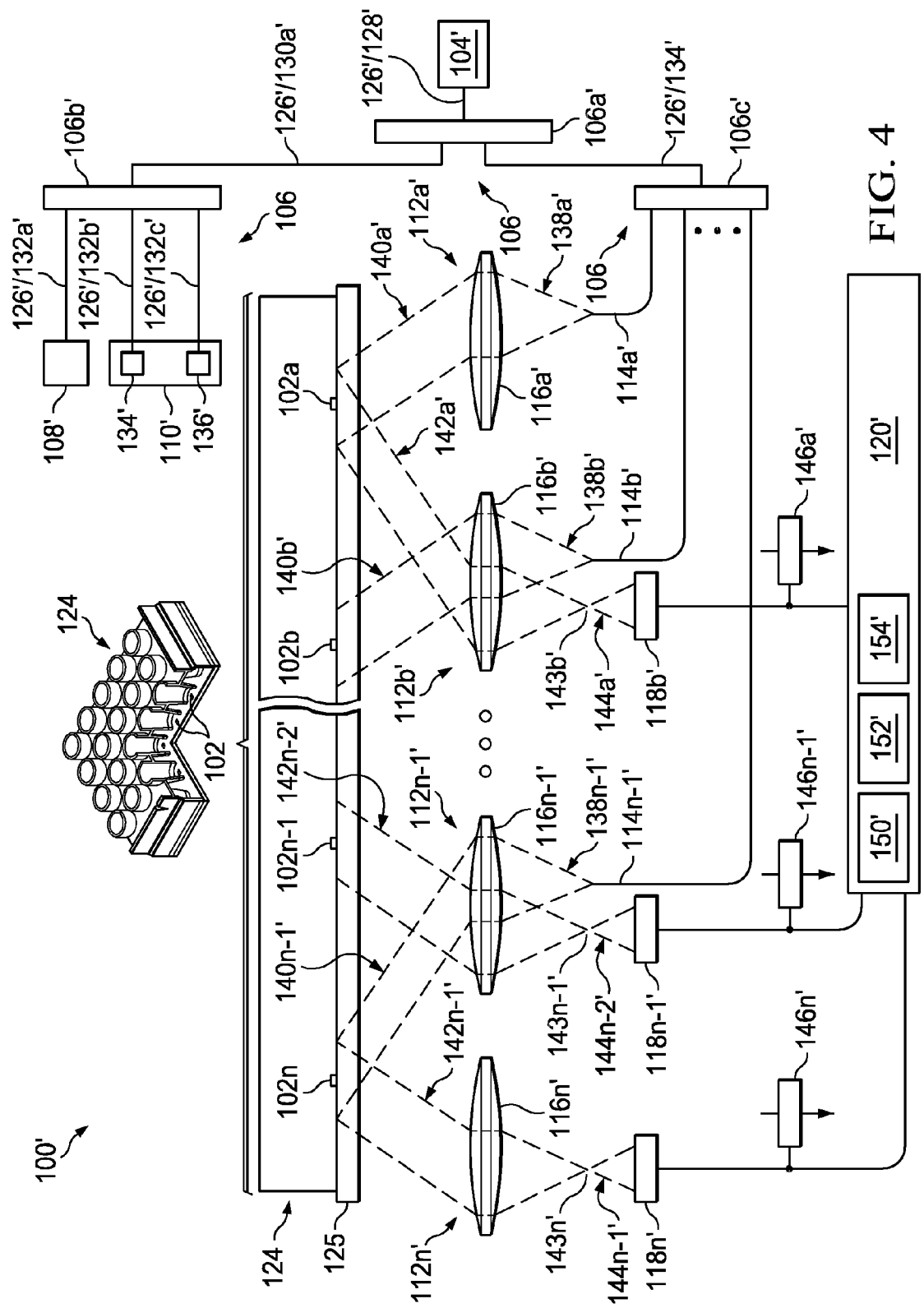
FIG. 4 is a block diagram of an exemplary optical interrogation system which is configured to interrogate one or more biosensors in accordance with another embodiment of the present invention.

Referring to FIG. 4, there is a block diagram illustrating the basic components of an exemplary optical interrogation system 100' which is configured to interrogate one or more biosensors 102*a*, 102*b* . . . 102*n* in accordance with another embodiment of the present invention. The exemplary optical interrogation system 100' is similar to the optical interrogation system 100 shown in FIG. 1 except that optical interrogation units 112*a'*, 112*b'* . . . 112*n'* as discussed below are configured differently than optical interrogation units 112*a*, 112*b* . . . 112*n*. As shown, the optical interrogation system 100' includes the tunable laser 104', the distribution unit 106' (e.g., 1×2 splitter 106*a'*, a 1×3 splitter 106*b'* and a 1×N splitter 106*c'*), the power tracking device 108', the wavelength tracking device 110', and the data processing device 120'. A discussion about different ways the optical interrogation system 100' can be used to interrogate the biosensors 102*a*, 102*b* . . . 102*n* is provided below with respect to methods 1000 and 1200 (see FIGS. 10 and 12).

In FIG. 4, the optical interrogation units 112*a'*, 112*b'* . . . 112*n'* are shown to include N-fiber launches 114*a'*, 114*b'* . . . 114*n*-1' (e.g., N single-mode fibers 114*a'*, 114*b'* . . . 114*n*-1') where each fiber launch 114*a'*, 114*b'* . . . 1014*n*-1' outputs an optical beam 138*a'*, 138*b'* . . . 138*n*-1' towards a corresponding collimating/imaging lens 116*a'*, 116*b'* . . . 116*n*-1' (note: the last lens 116*n'* is not coupled to a fiber launch). The lenses 116*a'*, 116*b'* . . . 116*n*-1' respectively collimate the optical beams 138*a'*, 138*b'* . . . 138*n*-1' and direct the collimated optical beams 140*a'*, 140*b'* . . . 140*n*-1' to illuminate and preferably overfill the corresponding biosensors 102*a*, 102*b* . . . 102*n*. The adjacent lenses 116*b'*, 116*c'* . . . 116*n'* receive the optical beams 142*a'*, 142*b'* . . . 142*n*-2', 142*n*-1' that are respectively reflected from the corresponding biosensors 102*a*, 102*b* . . . 102*n*. Then, the adjacent lenses 116*b'*, 116*c'* . . . 116*n'* emit an optical beam 144*a'*, 144*b'* . . . 144*n*-1' which are allowed to diverge beyond the focal points 143*b'*, 143*c'* . . . 143*n'* of the lenses 116*b'*, 116*c'* . . . 116*n'* so the optical beams 144*a'*, 144*b'* . . . 144*n*-1' form an image of the biosensors 102*a*, 102*b* . . . 102*a* on the corresponding photo detectors 118*b'* . . . 118*n*-1', 118*n'* (e.g., multiple element detectors 118*b'* . . . 118*n*-1', 118*n'* can be used to receive the sample spectra and reference spectra from corresponding biosensors 102*a*, 102*b* . . . 102*n*). If desired, the detectors 118*b'*, 118*c'* . . . 118*n'* can be positioned ahead of or on the focal points 143*a'*, 143*b'* . . . 143*n'* and still receive images of the biosensors 102*a*, 102*b* . . . 102*n*.

The detectors 118*b'*, 118*c'* . . . 118*n'* generate a sequence of intensity spot patterns 146*a'*, 146*b'* . . . 146*n'* from the respective biosensors 102*a*, 102*b* . . . 102*n* where each of the intensity spot patterns 146*a'*, 146*b'* . . . 146*n'* corresponds with one of the distinct wavelengths of the optical beam 126' that was emitted from the tunable laser 104'. For instance, detector 118*b'* generates a sequence of intensity spot patterns 146*a'* of the illuminated biosensor 102*a* where each intensity spot pattern 146*a'* corresponds with one of the distinct wavelengths of the optical beam 126' (and optical beam 138*a'*) that was emitted from the tunable laser 104' (and the fiber launch 114*a'*). The data processing device 120' receives and processes the collected intensity spot patterns 146*a'*, 146*b'* . . . 146*n'* to determine for example whether or not there was a biochemical interaction or some other event that occurred on one or more of the biosensors 102*a*, 102*b* . . . 102*n* or to calibrate a uniformity of surface chemistry and target molecule immobilizations on the one or more biosensors 102*a*, 102*b* . . . 102*n*.

Alternatively, the tunable laser 104' could emit an optical beam 126' that is distributed to the optical interrogation units 112*a'*, 112*b'* . . . 112*n'* using free space splitters or diffractive optics instead of the aforementioned fiber optic splitter 106*c'*. If the fiber optic splitter 106*c'* is used then the optical beam 126' could be passed through a polarization scrambler (not shown in FIG. 4) to eliminate the polarization effects of the single mode fibers 114*a'*, 114*b'* . . . 114*n*-1' in the optical interrogation units 112*a'*, 112*b'* . . . 112*n'*. FIG. 5 illustrates in greater detail optical interrogation units 112*a'* and 112*b'* where optical interrogation unit 112*a'* includes the single mode fiber launch 114*a'* that emits optical beam 138*a'* at lens 116*a'* (collimating optic 116*a'*) which emits a collimated optical beam 140*a'* that illuminates a transverse magnetic (TM) mode in the biosensor 102*a*. The biosensor 102*a* reflects a collimated optical beam 142*a'* which is received by the adjacent lens 116*b'* (part of optical interrogation unit 112*b'*) that outputs an optical beam 144*a'* which passes through a polarizer 502 (optional) and is incident upon photo detector 118*b'*. In this example, the fiber launch 114*a'* is located on a launch plane 503 at about 20 mm from the lens 116*a'* and the photo detector 118*b'* is located just below the focal point 144*a'* on an image plane about 7 mm from the adjacent lens 116*b'*. The lenses 116*a'* and 116*b'* are about 65 mm from the biosensor 102*a*.

The photo detector 118*b'* in this particular example is a multiple element photo detector since the biosensor 102*a* has both a sample region and a reference region but it could be a single element photo detector 118*b'* if the biosensor 102*a* had just a sample region and no reference region (see FIG. 3). The multiple element photo detector 118*b'* would be used in a self-referenced interrogation optics design where the photo detector 118*b'* could have two closely packaged photodiodes 504*a* and 504*b* that receive the interrogated beam 144*a'* from two halves of the grating in the biosensor 102*a*. The multiple element photo detector 118*b'* is therefore capable of detecting two channels to enable a self-referenced measurement. In one example, the multiple element photo detector 118*b'* can be made by Hamamastu Inc. and each photodiode 504*a* and 504*b* would be 1×1 mm$^2$ with a 20 μm gap between them. The imaging ratio would be about 3:1. For a detailed discussion about self-reference interrogation and an exemplary biosensor 102*a* which has a sample region and a reference region formed thereon reference is made to co-assigned U.S. Pat. No. 6,537,352 entitled "Method for Creating a Reference Region and a Sample Region on a Biosensor and the Resulting Biosensor". The contents of this particular document are hereby incorporated by reference herein.

Figure 6:
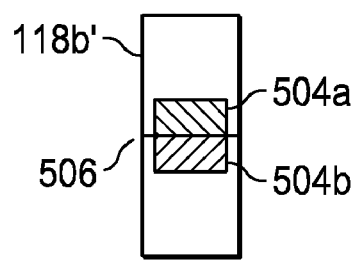
FIG. 6 is a top view of a two-element photo detector that could be incorporated within the optical interrogation systems shown in FIGS. 1 and 4 in accordance with an embodiment of the present invention.
Figure 7:
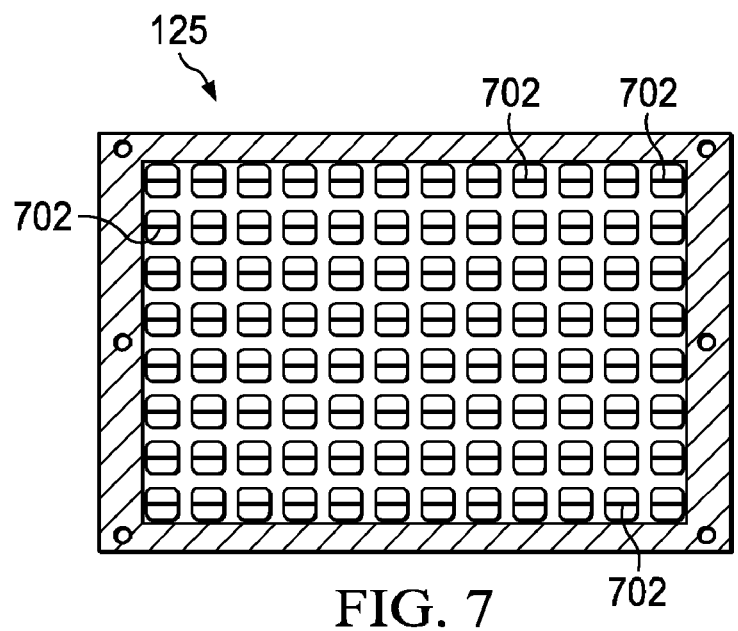
FIG. 7 is a diagram of a plate holder containing masks that can be used to support a microplate for the optical interrogation systems shown in FIGS. 1 and 4 in accordance with an embodiment of the present invention.
Figure 8:
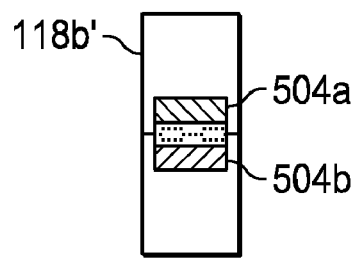
FIG. 8 is a diagram illustrating how a two-element photo detector with split photodiodes would look like when the plate holder which has masks is supporting the microplate in accordance with an embodiment of the present invention.

Referring to FIG. 6, there is shown a top view of a two-element photo detector 118*b'* with split photodiodes 504*a* and 504*b*. In this exemplary two-element photo detector 118*b'* where the grating of the biosensor 102*a* is directly imaged onto the split photodiodes 504a and 504b, the boundary between the signal and reference areas in the grating of the biosensor 102a needs to be exactly projected into the gap 506 of the two-element photo detector 118b', otherwise crosstalk occurs. However, when the center portion of the grating in the biosensor 102a is masked, then the signal area and reference area are reduced. Thus, if the biosensor 102a and the two-element photo detector 118b' are misaligned within the width of the mask then this would not result in the problematical crosstalk on the two-element photo detector 118b'. The mask can greatly increase the tolerance to the pitch errors of the component array as well as the assembly errors in the optical interrogation system 100 and 100'. In one embodiment, the masks 702 can be machined into the plate holder 125, as illustrated in FIG. 7. In one example, the typical width of each mask 702 is 0.6 mm in the holder 125 when a 2 mm wide grating is used in the biosensor 102a. FIG. 8 illustrates how the two-element photo detector 118b' with split photodiodes 504a and 504b would look like when a mask 702 was used on holder 125 which supports the microplate 124. The use of the mask 702 not only eliminates the problematical crosstalk on the two-element photo detector 118b', but also relaxes tolerances so various assembly methods can be used to assemble the different components of the optical interrogation system 100 and 100'.

Figure 9:
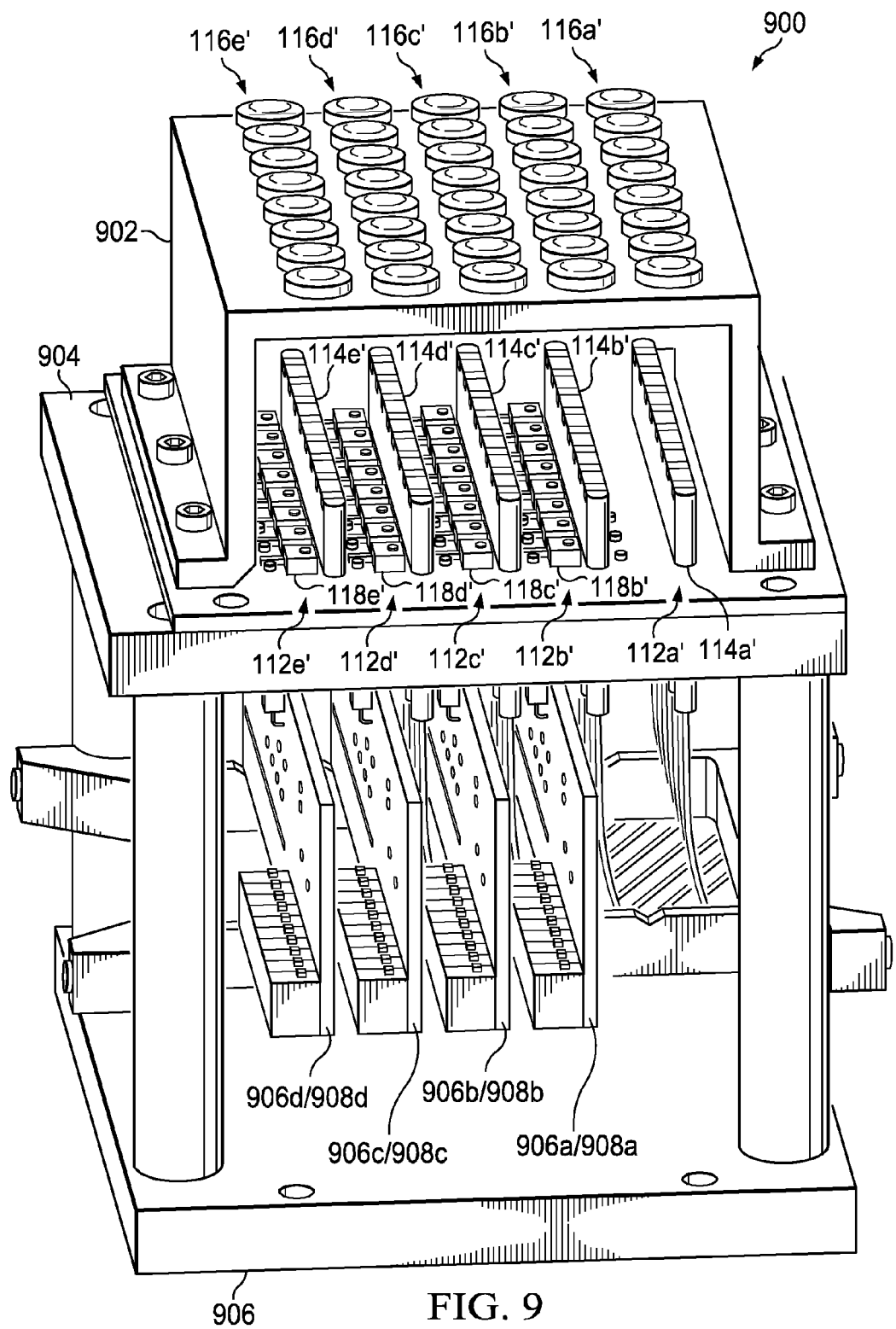
FIG. 9 is a diagram illustrating an optical reader head which is supporting an 5×8 array of optical interrogation units that can be incorporated into the optical interrogation system shown in FIG. 4 in accordance with an embodiment of the present invention.

Referring to FIG. 9, there is depicted an exemplary optical reader head 900 which has different supports 902, 904 and 906 that supports a 5×8 array of optical interrogation units 112a', 112b' ... 112e' including fiber launches 114a', 114b' ... 114e', lens 116a', 116b' ... 116e', and two-element photo detectors 118b', 118c' ... 118e'. An array of such optical reader heads 900 can be built with a repetitive pattern to match an entire microplate 124 or part of a microplate 124. For instance, to interrogate a 96 well microplate 124, three 5×8 optical reader heads 900 can be used which would make it easier to assemble the optical interrogation system 100. Plus, the array of optical interrogation units 112a', 112b' ... 112n' can be assembled using component arrays which have the desired pitch. The component arrays include an array of fiber launches 114a', 114b' ... 114n', an array of lenses 116a', 116b" ... 116n', and an array of photo detectors 118b', 118c' ... 118n'. The assembling of component arrays is easier than assembling individual components.

Furthermore, the optical reader head 900 can be mechanically connected to the plate holder 125 to form a rigid body. This configuration would yield a short mechanical distance between the optical interrogation system 100 and 100' and the microplate 124, and greatly improve the mechanical stability and the baseline stability of the optical interrogation system 100 and 100'. If the microplate 124 is a closed flow-through microplate with integrated fluidic micro channels then a fluidic interface can dock to the closed flow-through microplate when performing kinetic assays.

The exemplary optical interrogation system 100' has a configuration that is desirable since it effectively solves a problem where it is now possible to collect the optical signals 144a', 144b' ... 144n' from individual biosensors 102a, 102b ... 102n in the microplate 124 while enabling the detectors 118b', 118c' ... 118n' and the corresponding fiber launches 114a', 114b' ... 114n' to be positioned relatively close to one another. In the exemplary optical interrogation system 100, this can be a problem because the physical geometry and placement of the fiber launches 114a, 114b ... 114n and detectors 118a, 118b ... 118n would dictate the minimum separation possible. One potential solution to this problem would involve increasing the angle of incidence of the optical beams 140a, 140b ... 140n that are directed to the biosensors 102a, 102b ... 102n. However, the angle of incidence can only be increased to a point, otherwise vignetting will occur thereby compromising performance. The optical interrogation system 100' of the present invention effectively addresses this problem because it's configuration allows one to obtain a large separation between each pair of fiber launches 114a', 114b' ... 114n' and the detectors 118b', 118c' ... 118n' which increases the angle of incidence of the optical beams 1405', 140b' ... 140n' and avoids the problematical vingetting.

The optical interrogation system 100' has another desirable feature in that the reflected optical beams 142a', 142b' ... 142n' can be detected away from the launch plane or the image plane or at the image plane by the corresponding detectors 118b', 118c' ... 118n'. There are several advantages for detecting at the image plane: (1) the spot location does not shift with the tilt (or bow) of the microplate 124 therefore, this setup is insensitive to this parameter; and (2) the detectors 118b', 118c' ... 118n' are located at a different plane than the fiber launches 114a', 114b' ... 114n' thereby allowing more space for the detectors 118b', 118c' ... 118n'. In one example, the vertical distance between the fiber launches 114a', 114b' ... 114n' and the image planes can be about 7 mm, between the fiber launches 114a', 114b' ... 114n' and the lenses 116a', 116b' ... 116n' can be about 18 mm, and between the lenses 116a', 116b' ... 116n' and the microplate 124 can be about 65 mm.

In comparing the optical interrogation system 100 and the optical interrogation system 100' it should be noted that the optical interrogation system 100 has lenses 116a, 116b ... 116n which do not form a real image in the classical sense of the biosensors 102a, 102b ... 102n for any placement location of the detectors 118a, 118b ... 118n. In other words, the optical interrogation system 100 does not have an image plane beneath the lenses 116a, 116b ... 116n that corresponds to the biosensors 102a, 102b ... 102n above the lenses 116a, 116b ... 116n. However, it is true that at various locations of the detectors 118a, 118b ... 118n either ahead of or past the focal points 143a, 143b ... 143n of the lenses 116a, 116b ... 116n, the detectors 118a, 118b ... 118n can still "see" the biosensors 102a, 102b ... 102b (but not right at the focal points 143a, 143b ... 143n of the lenses 116a, 116b ... 116n). This is because the optical interrogation system 100 has a large "depth of focus" which is a result of the fact that there is only collimated light 142a, 142b ... 142n being reflected from the biosensors 102a, 102b ... 102n.

In contrast, the optical interrogation system 100' has a distance between the lenses 116a', 116b' ... 116n' and the microplate 124 that can be significantly larger than in the optical interrogation system 100 (compare FIGS. 3 and 5). Because of this increased distance the detectors 118b', 118c' ... 118n' can be located at the image plane, that is, the biosensors 102a, 102b ... 102n can be imaged onto the detectors 118b', 118c' ... 118n'. Again, it should be appreciated that the detectors 118b', 118c' ... 118n' could be positioned ahead of or after the image plane and still give a workable system. However, placing the detectors 118h', 118c' ... 118n' at the image plane is preferred since it results in an optical interrogation system 100' that is insensitive to the curvature of the microplate 124. Alternatively, if one were to build the optical interrogation system 100 then they could create the optical interrogation system 100 by adding another lens 116' and a detector 118' to receive the light 144n' from this lens 116' and by moving the microplate 1024 "up" and "to the right" (compare FIGS. 1 and 4).

Figure 10:
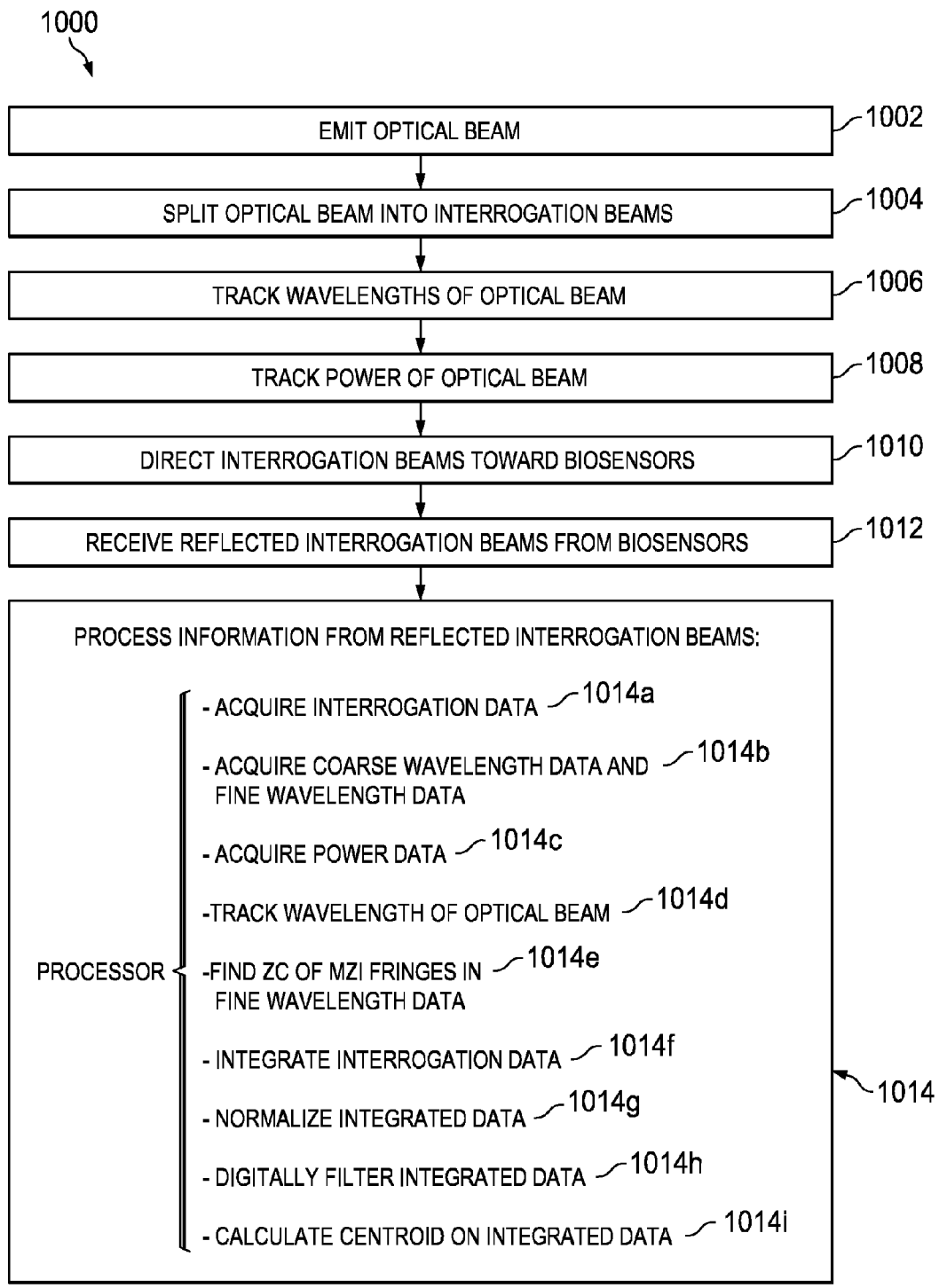
FIG. 10 is a flowchart illustrating the basic steps of a method for interrogating one or more biosensors in accordance with one embodiment of the present invention.

Referring to FIG. 10, there is illustrated the basic steps of a method 1000 for interrogating one or more biosensors 102a, 102b ... 102n in accordance with one embodiment of the present invention. At step 1002, the optical interrogation system 100 and 100' has a tunable laser 104 and 104' that emits an optical beam 126 and 126' which has a predetermined sequence of distinct wavelengths over a predetermined time period. At step 1004, the optical interrogation system 100 and 100' has a distribution unit 106 and 106' that splits the optical beam 126 and 126' into a plurality of interrogation beams 126 and 126'.

At step 1006, the optical interrogation system 100 and 100' has a wavelength tracking device 110 and 110' which tracks distinct wavelengths of the optical beam 126 and 126'. At step 1008, the optical interrogation system 100 and 100' has a power tracking device 108 and 108' which receives the optical beam 126 and 126' and tracks the power of the optical beam 126 and 126' emitted from the tunable laser 104 and 104'. At step 1010, the optical interrogation system 100 and 100' has an array of optical interrogation units 112a, 112b ... 112n and 112a', 112b' ... 112n' that receive and direct interrogation beams 138a, 138b ... 138n and 138a', 138b' ... 138n-1' towards an array of biosensors 102a, 102b ... 102n. At step 1012, the optical interrogation units 112a, 112b ... 112n and 112a', 112b' ... 112n' receive a plurality of reflected interrogation beams 144a, 144b ... 144n and 144a', 144b' ... 144n-1' from the biosensors 102a, 102b ... 102n.

At step 1014, the optical interrogation system 100 and 100' has a data processing device 120 and 120' that receives and processes information associated with the reflected interrogation beams 144a, 144b ... 144n and 144a', 144b' ... 144n-1'. A detailed discussion is provided next about how the data processing device 120 and 120' which includes a processor 150 and 150' and a memory 152 and 152' that stores processor-executable instructions where the processor 150 interfaces with the memory 150 and executes the processor-executable instructions to process information associated with the reflected interrogation beams 144a, 144b ... 144n and 144a', 144b' ... 144n-1', the wavelength data, and the power data to determine for example whether or not there was a biochemical interaction on anyone of the biosensors 102a, 102b ... 102n.

At step 1014a, the processor 150 and 150' acquires interrogation data obtained by one or more photo detectors 118a, 118b ... 118n and 118b', 118c' ... 118n' (part of the optical interrogation units 112a, 112b ... 112n and 112a', 112b' ... 112n') which receive the one or more reflected interrogation beams 144a, 144b ... 144n and 144a', 144b' ... 144n-1' from the one or more biosensors 102a, 102b ... 102n. For instance, the photo detectors 118a, 118b ... 118n and 118b', 118c' ... 118n' each output analog current which passes through a trans-impedance amplifier (TIA) 906a, 906b ... 906n before being converted to a digital signal (interrogation data) by an analog to digital converter (ADC) 908a, 908b ... 908n (see FIG. 9). The sampling rate of the ADCs 908a, 908b ... 908n can be 250 kHz to 1 MHz which is sufficient to enable kinetic assays.

At step 1014b, the processor and 150' acquires coarse wavelength data (associated with the etalon 136 and 136') and fine wavelength data (associated with the MZI interferometer 134 and 134') from the wavelength tracking device 110 and 110' which tracks distinct wavelengths of the optical beam 126 and 126' emitted from the tunable laser 104 and 104' (see FIGS. 2A-2B).

At step 1014c, the processor 150 and 150' acquires power data from the power tracking device 108 and 108' which tracks power of the optical beam 126 and 126' emitted from the tunable laser 104 and 104'. For instance, the processor 150 and 150' would acquire the interrogation data simultaneously with the coarse wavelength data, the fine wavelength data and the power data. In one embodiment, the processor 150 and 150' can process all of the acquired data as discussed below in steps 1014d-1014i after the laser scan is completed on the biosensors 102a, 102b ... 102n.

At step 1014d, the processor 150 and 150' tracks distinct wavelengths of the emitted optical beam 126 and 126' using the coarse wavelength data and the fine wavelength data. At step 1014e, the data processing device 120 and 120' finds instants of zero-crossings (ZC) of MZI fringes associated with the fine wavelength data where the frequency spacing between adjacent ZC points is FSR/2.

At step 1014f, the processor 150 and 150' integrates the interrogation data that was received between trigger points which correspond to adjacent instants of the zero-crossings of the MZI fringes associated with the fine wavelength data. Thus, the total number of integrated interrogation data is equal to the total number of ZC pairs.

At step 1014g, the processor 150 and 150' normalizes the integrated interrogation data using the power data from the power tracking device 108 and 108'. In one embodiment, the power tracking data is used to normalize the interrogated interrogation data and the MZI output so that these measurements are independent of the power variation in the tunable laser 104 and 104'.

Figure 11:
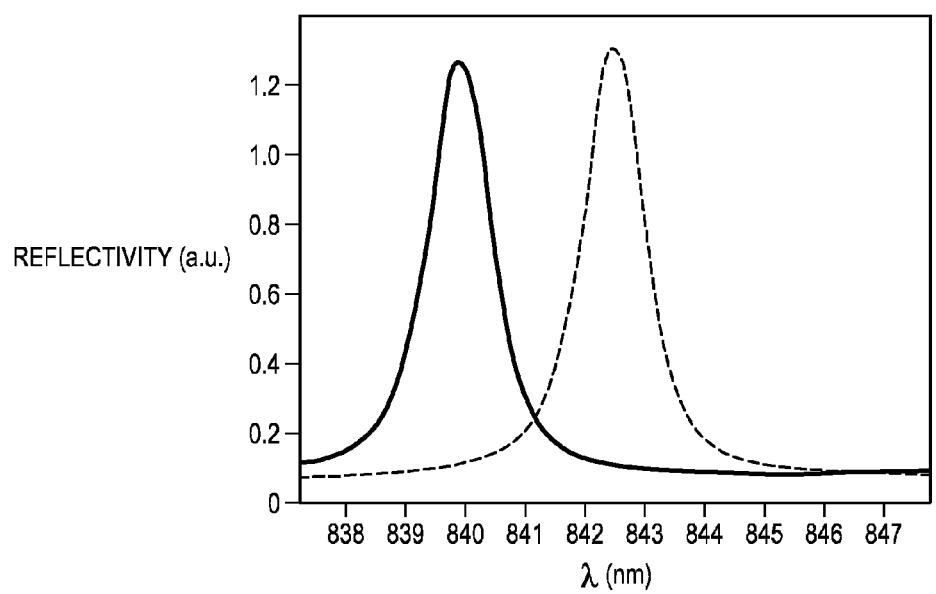
FIG. 11 is a graph illustrating exemplary interrogated grating spectra after performing a digital filtering step in the method shown in FIG. 10 in accordance with an embodiment of the present invention.

At step 1014h, the processor 150 and 150' digitally filters the normalized integrated interrogation data to remove the effect of the parasitic fringes that are caused by the grating substrates of the biosensors 102a, 102b ... 102n. Examples of interrogated grating spectra after undergoing the digital filtering are shown in FIG. 11. Plus, examples of several digital filtering techniques where discussed in the co-assigned U.S. Pat. No. 7,509,239 entitled "Optimized Method for LID Biosensor Resonance Detection". The contents of this document are hereby incorporated by reference herein.

At step 1014i, the processor 150 and 150' calculates a centroid for each digitally filtered normalized integrated interrogation data to determine a resonant wavelength for the one or more biosensors 102a, 102b ... 102n. In one embodiment, the resonant wavelength data can be used to determine whether or not there was a biochemical interaction on the one or more biosensors 102a, 102b ... 102n or for calibrating a uniformity of surface chemistry and target molecule immobilizations on the one or more biosensors 102a, 102b ... 102n. For instance, the processor 150 and 150' can acquire all of the data and determine the resonant wavelength for each of the biosensors 102a, 102b ... 102n at a data rate equal to or faster than 3 Hz and with a baseline noise of less than 100 fm.

The interrogation method 1000 works well but the large amount of data that needs to be acquired and processed may cause significant computation delays that limit the update rate of the optical interrogation system 100 and 100'. This is not desirable if the optical interrogation system 100 and 100' is used to perform kinetic assays with the biosensors 102a, 102b ... 102n. In this case, the data processing time should be faster than that of the laser sweep time over the biosensors 102a, 102b ... 102n. An example of how this can be accomplished is discussed below with respect to method 1200 shown in FIG. 12.

Figure 12:
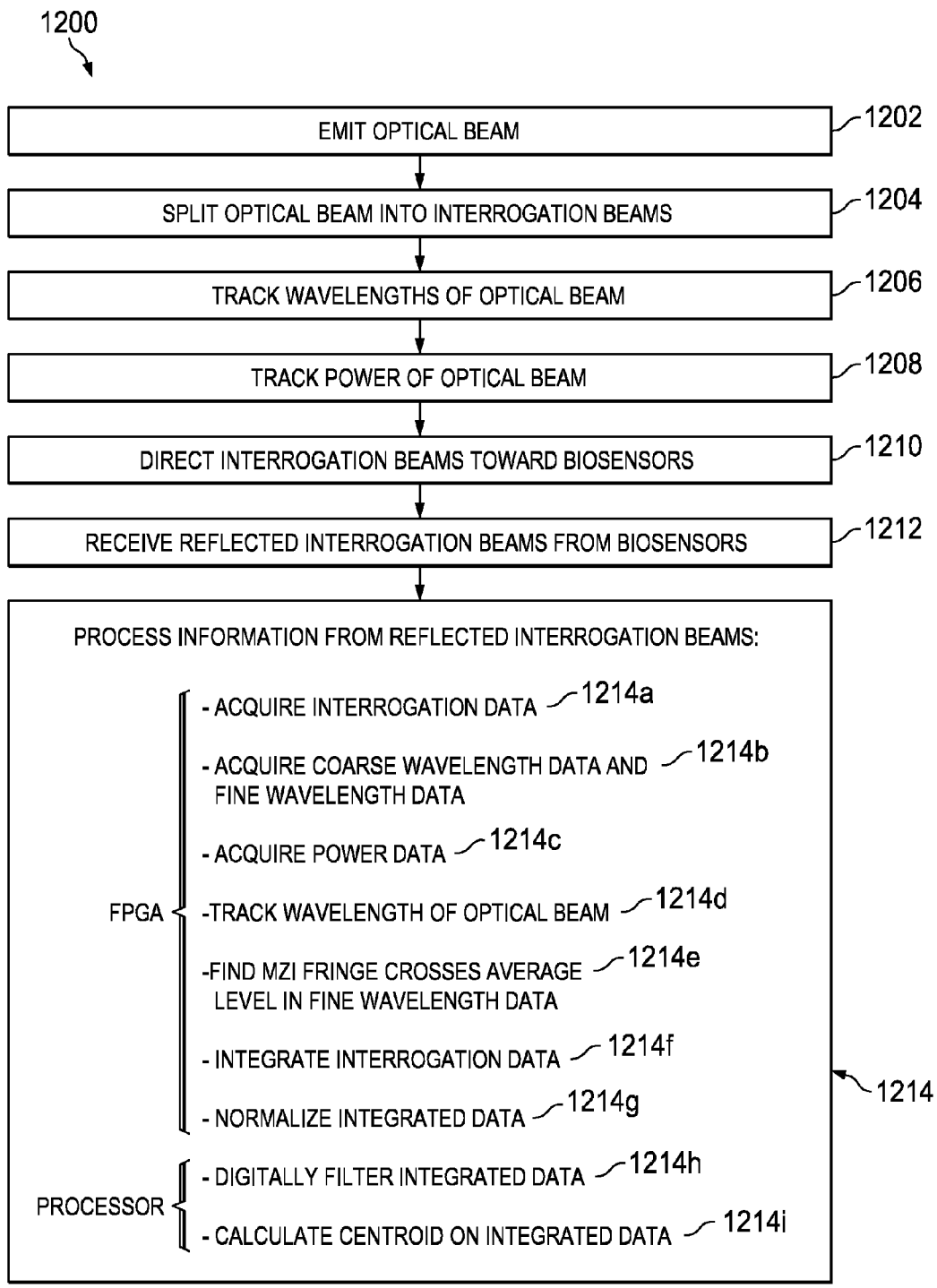
FIG. 12 is a flowchart illustrating the basic steps of a method for interrogating one or more biosensors in accordance with another embodiment of the present invention.

Referring to FIG. 12, there is illustrated the basic steps of a method 1200 for interrogating one or more biosensors 102a, 102b ... 102n in accordance with another embodiment of the present invention. At step 1202, the optical interrogation system 100 and 100' has a tunable laser 104 and 104' that emits an optical beam 126 and 126' which has a predetermined sequence of distinct wavelengths over a predetermined time period. At step 1204, the optical interrogation system 100 and 100' has a distribution unit 106 and 106' that splits the optical beam 126 and 126' into a plurality of interrogation beams 126 and 126'.

At step 1206, the optical interrogation system 100 and 100' has a wavelength tracking device 110 and 110' which tracks distinct wavelengths of the optical beam 126 and 126'. At step 1208, the optical interrogation system 100 and 100' has a power tracking device 108 and 108' which receives the optical beam 126 and 126' and tracks the power of the optical beam 126 and 126' emitted from the tunable laser 104 and 104'. At step 1210, the optical interrogation system 100 and 100' has an array of optical interrogation units 112a, 112b . . . 112n and 112a', 112b' . . . 112n' that receive and direct interrogation beams 138a, 138b . . . 138n and 138a', 138b' . . . 138n-1' towards an array of biosensors 102a, 102b . . . 102n. At step 1212, the optical interrogation units 112a, 112b . . . 112n and 112a', 112b' . . . 112n' receive a plurality of reflected interrogation beams 144a, 144b . . . 144n and 144a', 144b' . . . 144n-1' from the biosensors 102a, 102b . . . 102n.

At step 1214, the optical interrogation system 100 and 100' has a data processing device 120 and 120' that receives and processes information associated with the reflected interrogation beams 144a, 144b . . . 144n and 144a', 144b' . . . 144n-1'. A detailed discussion is provided next about how the data processing device 120 and 120' which in this embodiment includes a field programmable gate array (FPGA) processing board 154 and 154' (or an application specific integrated circuit (ASIC) 154 and 154') along with the processor 150 and 150' and the memory 152 and 152' can be used to process information associated with the reflected interrogation beams 144a, 144b . . . 144n and 144a', 144b' . . . 144n-1', the wavelength data and the power data to determine, for example, whether or not there was a biochemical interaction on anyone of the biosensors 102a, 102b . . . 102n.

At step 1214a, the FPGA processing board 154 and 154' acquires interrogation data obtained by one or more photo detectors 118a, 118b . . . 118n and 118b', 118c' . . . 118n' (part of the optical interrogation units 112a, 112b . . . 112n and 112a', 112b' . . . 112n') which receive the one or more reflected interrogation beams 144a, 144b . . . 144n and 144a', 144b' . . . 144n-1' from the one or more biosensors 102a, 102b . . . 102n. For instance, the photo detectors 118a, 118b . . . 118n and 118b', 118c' . . . 118n' each output analog current which passes through a trans-impedance amplifier (TIA) 906a, 906b . . . 906n before being converted to a digital signal (interrogation data) by an analog to digital converter (ADC) 908a, 908b . . . 908n (see FIG. 9). The sampling rate of the ADCs 908a, 908b . . . 908n can be 250 kHz to 1 MHz which is sufficient to enable kinetic assays.

At step 1214b, the FPGA processing board 154 and 154' acquires coarse wavelength data (associated with the etalon 136 and 136') and fine wavelength data (associated with the MZI interferometer 134 and 134') from the wavelength tracking device 110 and 110' which tracks distinct wavelengths of the optical beam 126 and 126' emitted from the tunable laser 104 and 104' (see FIGS. 2A-2B).

At step 1214c, the FPGA processing board 154 and 154' acquires power data from the power tracking device 108 and 108' which tracks power of the optical beam 126 and 126' emitted from the tunable laser 104 and 104'. For instance, the FPGA processing board 154 and 154' would acquire the interrogation data simultaneously with the coarse wavelength data, the fine wavelength data and the power data. At step 1214d, the FPGA processing board 154 and 154' tracks distinct wavelengths of the emitted optical beam 126 and 126' using the coarse wavelength data and the fine wavelength data.

Figure 13:
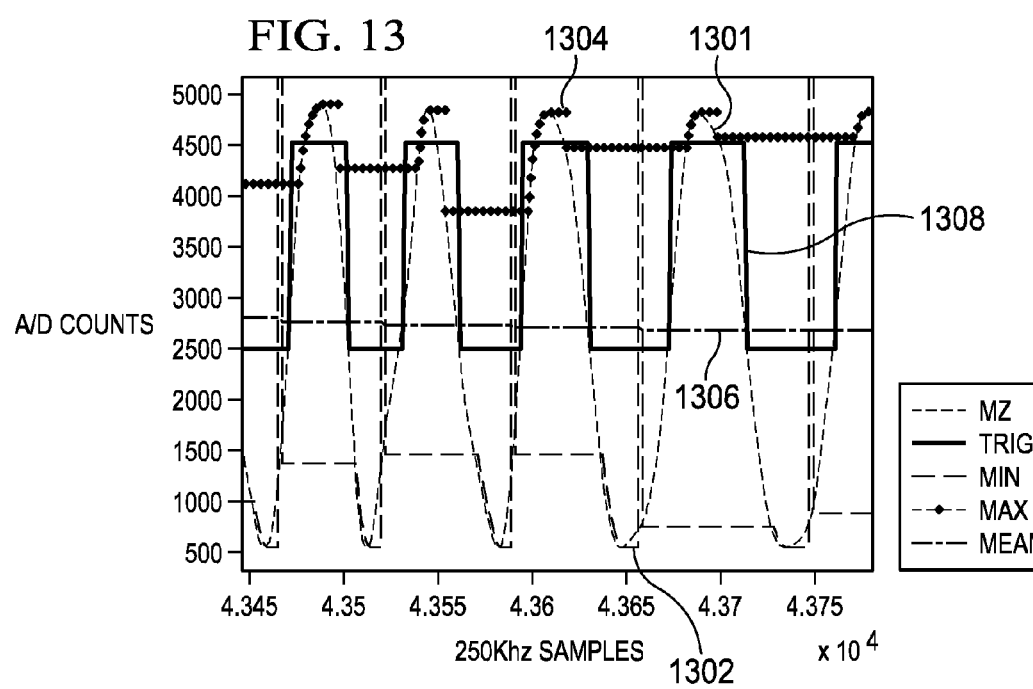
FIG. 13 is a graph used to explain how a field programmable gate array (FPGA) processing board can determine trigger points which are used to process interrogation data using the method shown in FIG. 12 in accordance with an embodiment of the present invention.

At step 1214e, the FPGA processing board 152 takes the fine wavelength data (MZI output) and generates in real time a trigger point at each instant when a MZI fringe associated with the fine wavelength data crosses an average level. An example of how this can be done is illustrated in FIG. 13, where as the laser wavelength sweeps, the output 1301 from the MZI 134 and 134' is digitized and input into the FPGA processing board 154 and 154' (step 1214b). Then, the FPGA processing board 154 and 154' locates the minimum level 1302 and the maximum level 1304 at each fringe period to predict the average level 1306. Thereafter, the FPGA processing board 154 and 154' generates the trigger points 1308 by comparing the current level of the MZI output 1301 with the predicted mean level 1306.

At step 1214f, the FPGA processing board 154 and 154' integrates the interrogation data that was received between the trigger points associated with the fine wavelength data. In one embodiment, the FPGA processing board 154 and 154' generates fewer trigger points when compared to the trigger points generated in step 1014g which increases the downstream processing rate. In tests, a continuous update rate of at least 7 Hz has been demonstrated with a baseline noise of <100 fm. This high data rate is important for resolving fast kinetic events.

At step 1214g, the FPGA processing board 154 and 154' normalizes the integrated interrogation data using the power data from the power tracking device 108 and 108'. In one embodiment, the power tracking data is used to normalize the interrogated interrogation data and the MZI output so that these measurements are independent of the power variation of the tunable laser 104 and 104'.

At step 1214h, the processor 150 and 150' digitally filters the normalized integrated interrogation data to remove the effect of the parasitic fringes that are caused by the grating substrates of the biosensors 102a, 102b . . . 102n. Examples of several digital filtering techniques where discussed in the co-assigned U.S. Pat. No. 7,509,239 entitled "Optimized Method for LID Biosensor Resonance Detection". The contents of this document are hereby incorporated by reference herein.

At step 1214i, the processor 150 and 150' calculates a centroid for each digitally filtered normalized integrated interrogation data to determine a resonant wavelength for the one or more biosensors 102a, 102b . . . 102n. In one embodiment, the resonant wavelength data can be used to determine whether or not there was a biochemical interaction on the one or more biosensors 102a, 102b . . . 102n or for calibrating a uniformity of surface chemistry and target molecule immobilizations on the one or more biosensors 102a, 102b . . . 102n.

From the foregoing, optical interrogation systems 100 and 100' have been described which can be used to interrogate an array of resonance waveguide grating biosensors 102a, 102b . . . 102n. The optical interrogation systems 100 and 100' include a broadly tunable swept wavelength external cavity tunable laser 104 and 104', a power tracking device 108 and 108', a wavelength tracking device 110 and 110, an array of interrogation optics 112a, 112b . . . 112n and 112a', 112b' . . . 112n', and an array of photo detectors 118a, 118b . . . 118n and 118b', 118c' . . . 118n'. The photo detectors 118a, 118b . . . 118n and 118b', 118c' . . . 118n' can be photodiodes which are able to receive a much larger amount of optical power without saturation when compared to image sensors. Therefore, the shot noise limit of a photodiode based optical interrogation system 100 and 100' is inherently superior than an image based optical interrogation system. Plus, the amount of data from discrete array of photo diodes is significantly smaller than that of an imaging based system which makes the data processing software both simpler and faster.

Although multiple embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

The invention claimed is:

1. An optical interrogation system comprising:
a tunable laser that emits an optical beam which has a predetermined sequence of distinct wavelengths over a predetermined time period;
a distribution unit that splits the optical beam into a plurality of interrogation beams;
an array of optical interrogation units that receive and direct the interrogation beams towards an array of biosensors, wherein each of the optical interrogation units receives one of the interrogation beams and directs the one interrogation beam to one of the biosensors, wherein each biosensor has a signal area and a reference area, and wherein each optical interrogation unit further includes a photo detector with two photodiodes;
said array of optical interrogation units receive a plurality of reflected interrogation beams from the array of biosensors, wherein each of the optical interrogation units receives a directed one interrogation beam as a reflected interrogation beam from one of the biosensors;
a data processing device that receives and processes information associated with the reflected interrogation beams; and
a holder that supports the array of biosensors where said holder includes an array of masks, wherein each of the masks blocks a portion of one of the biosensors from being illuminated by one of the interrogation beams, wherein the portion is a central portion between the signal area and the reference area of the one biosensor, and wherein each mask blocks one of the reflected interrogation beams off the corresponding one biosensor from illuminating a gap between the two photodiodes of the photo detectors of the corresponding optical interrogation unit.

2. The optical interrogation system of claim 1, further comprising a wavelength tracking device that tracks the distinct wavelengths of the optical beam emitted from said tunable laser.

3. The optical interrogation system of claim 2, wherein said wavelength tracking device further comprises a Mach-Zehnder interferometer and an etalon.

4. The optical interrogation system of claim 1, further comprising a power tracking device that tracks the power of said tunable laser.

5. The optical interrogation system of claim 1, wherein said array of optical interrogation units further comprises a first optical interrogation unit that includes:
a first fiber launch that receives a first interrogation beam from said distribution unit and outputs the first interrogation beam;
a first lens that collimates the first interrogation beam outputted from said first fiber launch where the collimated interrogation beam illuminates a first biosensor;
said first lens receives a first reflected interrogation beam from the first biosensor; and
a first photo detector that receives the first reflected interrogation beam output from said first lens.

6. The optical interrogation system of claim 5, wherein said first photo detector is located ahead or past a focal point of said first lens.

7. The optical interrogation system of claim 5, wherein said first optical interrogation unit further includes a polarizer through which passes either or both the first interrogation beam and the first reflected interrogation beam.

8. The optical interrogation system of claim 1, wherein said array of optical interrogation units further comprises a first optical interrogation unit that includes:
a first fiber launch that receives a first interrogation beam from said distribution unit and outputs the first interrogation beam;
a first lens that collimates the first interrogation beam outputted from said first fiber launch where the collimated interrogation beam illuminates a first biosensor;
said first lens receives a second reflected interrogation beam from a second biosensor; and
a first photo detector that receives the second reflected interrogation beam output from said first lens.

9. The optical interrogation system of claim 8, wherein said first photo detector is located ahead or past a focal point of said first lens.

10. The optical interrogation system of claim 8, wherein said first optical interrogation unit further includes a polarizer through which passes either or both the first interrogation beam and the second reflected interrogation beam.

11. The optical interrogation system of claim 1, wherein said array of biosensors are located within an array of wells in a microplate.

12. The optical interrogation system of claim 1, wherein said array of optical interrogation units are located in a mechanical housing connected to the holder that supports the array of biosensors.

13. An optical interrogation system comprising:
a tunable laser that emits an optical beam which has a predetermined sequence of distinct wavelengths over a predetermined time period;
a distribution unit that splits the optical beam into a plurality of interrogation beams;
an array of optical interrogation units that receive and direct the interrogation beams towards an array of biosensors, wherein each of the optical interrogation units receives one of the interrogation beams and directs the one interrogation beam to one of the biosensors;
said array of optical interrogation units receive a plurality of reflected interrogation beams from the array of biosensors, wherein each of the optical interrogation units receives a directed one interrogation beam as a reflected interrogation beam from one of the biosensors; and
a data processing device that receives and processes information associated with the reflected interrogation beams, wherein said data processing device further includes a memory that stores processor-executable instructions and a processor that interfaces with the memory and executes the processor-executable instructions to:
acquire interrogation data obtained by a plurality of photo detectors in said plurality of optical interrogation units where said plurality of photo detectors receive the plurality of reflected interrogation beams from the array of bio sensors;
acquire coarse wavelength data and fine wavelength data from a wavelength tracking device;
acquire power data from a power tracking device which tracks the power of said tunable laser;

track distinct wavelengths of the optical beam emitted from said tunable laser using the coarse wavelength data and the fine wavelength data;

find instants of zero-crossings of fringes associated with the fine wavelength data;

integrate the interrogation data for each biosensor that was received between trigger points which correspond to adjacent instants of the zero-crossings of the fringes associated with the fine wavelength data;

normalize the integrated interrogation data using the power data from the power tracking device;

digitally filter the normalized integrated interrogation data; and calculate a centroid for each digitally filtered normalized integrated interrogation data to determine a resonant wavelength for each of the biosensors.

14. The optical interrogation system of claim 13, wherein said processor acquires all of the data and determines the resonant wavelength for each of the biosensors at a data rate equal to or faster than 3 Hz and with a baseline noise of less than 100 fm.

15. An optical interrogation system comprising:

a tunable laser that emits an optical beam which has a predetermined sequence of distinct wavelengths over a predetermined time period;

a distribution unit that splits the optical beam into a plurality of interrogation beams;

an array of optical interrogation units that receive and direct the interrogation beams towards an array of biosensors, wherein each of the optical interrogation units receives one of the interrogation beams and directs the one interrogation beam to one of the biosensors;

said array of optical interrogation units receive a plurality of reflected interrogation beams from the array of biosensors, wherein each of the optical interrogation units receives a directed one interrogation beam as a reflected interrogation beam from one of the biosensors; and a data processing device that receives and processes information associated with the reflected interrogation beams, wherein said data processing device further includes a field programmable gate array, FPGA, processing board or an application specific integrated circuit, ASIC, which is used to:

acquire interrogation data obtained by a plurality of photo detectors in said plurality of optical interrogation units where said plurality of photo detectors receive the plurality of reflected interrogation beams from the array of bio sensors;

acquire coarse wavelength data and fine wavelength data from a wavelength tracking device;

acquire power data from a power tracking device which tracks the power of said tunable laser;

track distinct wavelengths of the optical beam emitted from said tunable laser using the coarse wavelength data and the fine wavelength data;

generate a trigger point at each instant when a fringe associated with the fine wavelength data crosses an average level where the average level is determined by using a minimum level and a maximum level of a previous fringe period to compute a predicted average level and then comparing a level of a current fringe with the predicted average level;

integrate the interrogation data for each biosensor that was received between each pair of trigger points which are associated with the fine wavelength data; and normalize the integrated interrogation data using the power data from the power tracking device;

said data processing device further includes a memory that stores processor-executable instructions and a processor that interfaces with the memory and executes the processor-executable instructions to:

digitally filter the normalized integrated interrogation data; and calculate a centroid for each digitally filtered normalized integrated interrogation data to determine a resonant wavelength for each of the biosensors.

16. The optical interrogation system of claim 15, wherein said FPGA processing board or said ASIC and said processor acquire all of the data and determine the resonant wavelength for each of the biosensors at a data rate equal to or faster than 7 Hz and with a baseline noise of less than 100 fm.

17. A method for interrogating one or more biosensors, said method comprising the steps of:

emitting, from a tunable laser, an optical beam which has a predetermined sequence of distinct wavelengths over a predetermined time period;

splitting, at a distribution unit, the optical beam into one or more interrogation beams;

directing, from an array of optical interrogation units, the one or more interrogation beams towards one or more biosensors, wherein each of the optical interrogation units receives one of the interrogation beams and directs the one interrogation beam to one of the biosensors, wherein each biosensor has a signal area and a reference area, and wherein each optical interrogation unit further includes a photo detector with two photodiodes;

receiving, at the array of optical interrogation units, one or more reflected interrogation beams from the one or more biosensors, wherein each of the optical interrogation units receives a directed one interrogation beam as a reflected interrogation beam from one of the biosensors;

processing information associated with the reflected interrogation beams; and said array of biosensors are supported by a holder which includes an array of masks, wherein each of the masks blocks a portion of one of the biosensors from being illuminated by one of the interrogation beams, wherein the portion is a central portion between the signal area and the reference area of the one biosensor, and wherein each mask blocks one of the reflected interrogation beams off the corresponding one biosensor from illuminating a gap between the two photodiodes of the photo detectors of the corresponding optical interrogation unit.

18. The method of claim 17, wherein said step of processing further includes:

determining whether or not there was a biochemical interaction on the one or more biosensors; or calibrating a uniformity of surface chemistry and target molecule immobilizations on the one or more biosensors.

19. A method for interrogating one or more biosensors, said method comprising the steps of:

emitting, from a tunable laser, an optical beam which has a predetermined sequence of distinct wavelengths over a predetermined time period;

splitting, at a distribution unit, the optical beam into one or more interrogation beams;

directing, from an array of optical interrogation units, the one or more interrogation beams towards one or more biosensors, wherein each of the optical interrogation units receives one of the interrogation beams and directs the one interrogation beam to one of the biosensors, wherein each biosensor has a signal area and a reference area, and wherein each optical interrogation unit further includes a photo detector with two photodiodes;

receiving, at the array of optical interrogation units, one or more reflected interrogation beams from the one or more biosensors, wherein each of the optical interrogation units receives a directed one interrogation beam as a reflected interrogation beam from one of the biosensors;

processing information associated with the reflected interrogation beams; wherein said step of processing further includes the steps of:

acquiring interrogation data obtained by one or more photo detectors which receive the one or more reflected interrogation beams from the one or more biosensors;

acquiring coarse wavelength data and fine wavelength data from a wavelength tracking device;

acquiring power data from a power tracking device which tracks the power of the emitted optical beam;

tracking distinct wavelengths of the emitted optical beam using the coarse wavelength data and the fine wavelength data;

finding instants of zero-crossings of fringes associated with the fine wavelength data; integrating the interrogation data for each biosensor that was received between trigger points which correspond to adjacent instants of the zero-crossings of the fringes associated with the fine wavelength data;

normalizing the integrated interrogation data using the power data from the power tracking device;

digitally filtering the normalized integrated interrogation data; and calculating a centroid for each digitally filtered normalized integrated interrogation data to determine a resonant wavelength for the one or more biosensors.

20. A method for interrogating one or more biosensors, said method comprising the steps of:

emitting, from a tunable laser, an optical beam which has a predetermined sequence of distinct wavelengths over a predetermined time period;

splitting, at a distribution unit, the optical beam into one or more interrogation beams;

directing, from an array of optical interrogation units, the one or more interrogation beams towards one or more biosensors, wherein each of the optical interrogation units receives one of the interrogation beams and directs the one interrogation beam to one of the biosensors, wherein each biosensor has a signal area and a reference area, and wherein each optical interrogation unit further includes a photo detector with two photodiodes;

receiving, at the array of optical interrogation units, one or more reflected interrogation beams from the one or more biosensors, wherein each of the optical interrogation units receives a directed one interrogation beam as a reflected interrogation beam from one of the biosensors;

processing information associated with the reflected interrogation beams; wherein said step of processing further includes the steps of:

acquiring interrogation data obtained by one or more photo detectors which receive the one or more reflected interrogation beams from the one or more biosensors;

acquiring coarse wavelength data and fine wavelength data from a wavelength tracking device;

acquiring power data from a power tracking device which tracks power of the emitted optical beam;

tracking distinct wavelengths of the emitted optical beam using the coarse wavelength data and the fine wavelength data;

generating a trigger point at each instant when a fringe associated with the fine wavelength data crosses an average level where the average level is determined by using a minimum level and a maximum level of a previous fringe period to compute a predicted average level and then comparing a level of a current fringe with the predicted average level;

integrating the interrogation data for each biosensor that was received between each pair of trigger points which are associated with the fine wavelength data; and normalizing the integrated interrogation data using the power data from the power tracking device;

digitally filtering the normalized integrated interrogation data; and calculating a centroid for each digitally filtered normalized integrated interrogation data to determine a resonant wavelength for the one or more biosensors.

21. The method of claim 17, wherein said one or more biosensors are located within a microplate which is used to perform an endpoint or kinetic biochemical assay.

* * * * *